(12) United States Patent
Ekwuribe

(10) Patent No.: US 6,638,906 B1
(45) Date of Patent: Oct. 28, 2003

(54) AMPHIPHILIC POLYMERS AND POLYPEPTIDE CONJUGATES COMPRISING SAME

(75) Inventor: Nnochiri Ekwuribe, Cary, NC (US)

(73) Assignee: Nobex Corporation, Research Triangle Park, NC (US)

( * ) Notice: Subject to any disclaimer, the term of this patent is extended or adjusted under 35 U.S.C. 154(b) by 0 days.

(21) Appl. No.: 09/459,443

(22) Filed: Dec. 13, 1999

(51) Int. Cl.[7] .............................................. A01N 37/18

(52) U.S. Cl. ............................. 514/2; 514/2; 514/21; 514/8; 530/350; 530/300; 530/303

(58) Field of Search ................... 514/2, 21, 8; 530/350, 530/300, 303

(56) References Cited

U.S. PATENT DOCUMENTS

| | | | |
|---|---|---|---|
| 5,359,030 A | * 10/1994 | Ekwuribe | 530/303 |
| 5,407,683 A | 4/1995 | Shively | 424/439 |
| 5,422,364 A | 6/1995 | Nicolaou et al. | 514/449 |
| 5,438,040 A | 8/1995 | Ekwuribe | 514/3 |
| 5,439,686 A | 8/1995 | Desai et al. | 424/451 |
| 5,484,809 A | 1/1996 | Hostetler et al. | 514/449 |
| 5,560,933 A | 10/1996 | Soon-Shiong et al. | 424/489 |
| 5,608,087 A | 3/1997 | Nicolaou et al. | 549/510 |
| 5,681,811 A | * 10/1997 | Ekwuribe | 514/8 |
| 5,795,909 A | 8/1998 | Shashoua et al. | 514/449 |
| 5,817,840 A | 10/1998 | Nicolaou et al. | 549/510 |
| 5,932,462 A | 8/1999 | Harris et al. | 435/188 |
| 6,191,105 B1 | 2/2001 | Ekwuribe et al. | 514/3 |
| 6,309,633 B1 | 10/2001 | Ekwuribe et al. | 424/85.1 |

FOREIGN PATENT DOCUMENTS

| | | | |
|---|---|---|---|
| WO | WO 97/04796 | * 2/1997 | |
| WO | WO97/15671 | 5/1997 | C12N/15/16 |
| WO | WO 97/33552 | 9/1997 | |
| WO | WO 98/58927 | 12/1998 | |

OTHER PUBLICATIONS

Adams, Jonathan D., et al. "Taxol: A History of Pharmaceutical Development and Current Pharmaceutical Concerns." J. Natl Cancer Inst Monographs (1993) 15:141–147.
Arbuck, S.G. "Taxol (paclitaxel): Future directions." Annals of Oncology (1994) 5(Suppl 6): S59–S62.
Beijnen, Jos H., et al. "Bioanalysis, Pharmacokinetics, and Pharmacodynamics of the Novel Anticancer Drug Paclitaxel (Taxol)." Sem in Oncology (1994) 21 (5) (Supp 8 Oct.) 53–62.
Deutsch, H.M., et al. "Synthesis of Congeners and Prodrugs. 3.[1] Water–Soluble Prodrugs of Taxol with Potent Antitumor Activity." J Medicinal Chem (1989) 32: 788–792.
Greenwald, R.B., et al. "Drug Delivery Systems: Water Soluble Taxol 2'–Poly(ethylene) glycol) Ester Prodrugs— Design and in Vivo Effectiveness." J. Medicinal Chem (1996) 39:424–431.
Greenwald, R.B. et al. "Highly Water Soluble Taxol Derivatives: 7–Polyethylene Glycol Carbamates and Carbonates." J Org Chem (1995) 60: 331–336.
Horwitz, S.B. "Taxol (paclitaxel): Mechanisms of action." Annals of Oncology (1994) 5 (Suppl.6): S3–S6.
Kingston, David G.I. "Taxol: the chemistry and structure–activity relationships of a novel anticancer agent." TIBTECH (Jun. 1994) 12: 222–227.
Kingston, David G.I. "The Chemistry of Taxol." Pharmac Ther (1991) 52: 1–33.
Kohler, David R., et al. "Paclitaxel (Taxol)." (1994) Pharmacotherapy 14 (1): 3–34.
Long, Harry J. "Paclitaxel (Taxol): A Novel Anticancer Chemotherapeutic Drug." Mayo Clin Proc (1994) 69:341–345.
Parekh, H. et al. "The Transport and Binding of Taxol." Gen Pharmac (1997) 29(2): 167–172.
Preston, N.J. "Paclitaxel (Taxol)—a guide to administration." European J of Cancer Care (1996) 5: 147–152.
Rowinsky, Eric K. et al. "The Clinical Pharmacology and Use of Antimicrotubule Agents in Cancer Chemotherapeutics." Pharmac Ther (1991) 52: 35–84.
Rowinsky, Eric K. et al. "Taxol: The First of the Taxanes, an Important New Class of Antitumor Agents." Seminars in Oncology (1992 Dec.) 19(6):646–662.
Rowinsky, Eric K. et al. "Taxol: Pharmacology, Metabolism and Clinical Implications." Cancer Surveys (1993) 17:283–304.
Straubinger, Robert M. et al. "Novel Taxol Formulations: Taxol–Containing Liposomes." J Nat Cancer Inst Monographs (1993) No. 15: 69–78.
Workman, Paul. "Pharmacokinetics and Cancer: Successes, Failures and Future Prospects." Cancer Surveys (1993) 17: 1–26.
Delgado et al. "The Uses and Properties of PEG–Linked Proteins". *Critical Review in Therapeutic Drug Carrier Systems*, 9(3,4):249–304 (1992).
Anderson et al., "Structure–Activity Relationship Assessment of Conjugated Enkephalins in Centrally Mediated Analgesia," *Soc. Neurosci. Abstr.*, 25(1): 180 (1999). (Abstract).
Ekwuribe et al., "Oral Insulin Delivery: Hydrolyzable Amphiphilic Oligomer Conjugates Prolong Glucose Reduction," *Proceed. Int'l. Symp. Control. Rel. Bioact. Mater.*, 26:147–148 (1999).

(List continued on next page.)

*Primary Examiner*—Christopher S. F. Low
*Assistant Examiner*—Hope A. Robinson
(74) *Attorney, Agent, or Firm*—Myers Bigel Sibley & Sajovec, P.A.; William A. Barrett, Esq.

(57) ABSTRACT

Proteins and/or peptides, such as luminal cholecystokinin releasing factor (LCRF), are conjugated with amphiphilic oligomers and polymers. Such conjugates may modulate the pharmacokinetic profile and/or peptides; thereby improving their clinical utility. Such conjugates may also stabilize and deliver the proteins and/or peptides, such as LCRF, to receptors in the gut without absorption into the bloodstream.

21 Claims, 3 Drawing Sheets

OTHER PUBLICATIONS

Freeman et al., "Interactions of Pancreatic Secretory Trypsin Inhibitor in Small Intestinal Juice: Its Hydrolysis and Protection by Intraluminal Factors," *Clinica Chimica Acta*, 195: 27–40 (1990).

Friedman, J. & Halaas, J., "Leptin and the Regulation of Body Weight in Mammals," *Nature*, 395:763–770 (1998).

Grant et al., "Development of Neuroendocrine Tumors in the Gastrointestinal Tract of Transgenic Mice. Heterogeneity of Hormone Expression," *Am. J. Pathol.*, 136(6): 1349–1363 (1990). (Abstract).

Green, G. & Lyman, R., "Feedback Regulation of Pancreatic Enzyme Secretion as a Mechanism for Trypsin Inhibitor–Induced Hypersecretion in Rats," *Proceedings of the Society for Experimental Biology and Medicine*, 140(1): 6–12 (1972).

Green et al., "Plasma Secretin, CCK, and Pancreatic Secretion in Response to Dietary Fat in the Rat," *Am. J. Physiol.*, 256: G1016–1021 (1989). (Abstract).

Gary M. Green, "Feedback Inhibition of Cholecystokinin Secretion by Bile Acids and Pancreatic Proteases," *Annals New York Academy of Sciences*, 713: 167–179 (1994).

Herzig et al., "Diazepam Binding Inhibitor is a Potent Cholecystokinin–Releasing Peptide in the Intestine," *Proc. Natl. Acad. Sci. USA*, 93:7927–7932 (1996).

Jin et al., "Roles of Gut Hormones in Negative–Feedback Regulation of Pancreatic Exocrine Secretion in Humans," *Gastroenterology*, 107: 1828–1834 (1994).

Krishnan et al., "Oral Delivery of Calcitonin by Conjugation with Amphiphilic Oligomers," *Proceed. Int'l. Symp. Control. Rel. Bioact. Mater.*, 26: 149–150 (1999).

Layer et al., "Feedback Regulation of Human Pancreatic Secretion," *Gastroenterology*, 98: 1311–1319 (1990).

Li, Y. & Owyang, C., "Peptone Stimulates CCK–Releasing Peptide Secretion by Activating Intestinal Submucosal Cholinergic Neurons," *J. Clin. Invest.*, 97(6): 1463–1470 (1996).

Rodger A. Liddle, "Regulation of Cholecystokinin Gene Expression in Rat Intestine," *Annals of the New York Academy of Sciences*, 713: 22–31 (1994).

Rodger A. Liddle, "Cholecystokinin Cells," *Annu. Rev. Physiol.*, 59: 221–242 (1997).

Liddle et al., "Luminal Cholecystokinin Releasing Factor (LCRF) Stimulates CCK Release from Intestinal Endocrine Cells Through a Calcium Influx Pathway," *Gatroenterology*, 116(4):A622 (1999). (Abstract).

Lu et al., "A Cholecystokinin Releasing Peptide Mediates Feedback Regulation of Pancreatic Secretion," *Am. J. Physiol.*, 256: G430–435 (1989). (Abstract).

Mangel et al., "Phenylalanine–Stimulated Secretion of Choloecystokinin is Calcium Dependent," *American Journal of Physiology: Gastrointestinal and Liver Physiology*, 31(1): G90–G94 (1995).

Miyasaka, K. & Funakoshi, A., "Luminal Feedback Regulation, Monitor Peptide, CCK–Releasing Peptide, and CCK Receptors," *Pancreas*, 16(3): 277–283 (1998).

Miyasaka et al., "Feedback Regulation by Trypsin: Evidence for Intraluminal CCK–Releasing Peptide," *Am. J. Physiol.*, 257: G175–181 (1989). (Abstract).

Viktor Mutt, "Secretin and Cholecystokinin," *Advances in Metabolic Disorders*, 11: 251–320 (1988).

Parlesak et al., "Parallel Determination of Gut Permeability in Man with $M_r$ 400, $M_r$ 1500, $M_r$ 4000,and $M_r$ 10 000, Polyethylene Glycol)," *Eur. J. Clin. Chem. Clin. Biochem.*, 32: 813–820 (1994).

Prpic et al., "Inhibition of $Na^+/H^+$ Exchange Stimulates CCK Secretion in STC–1 Cells," *Am. J. Physiol.*, 275: G689–695 (1998).

Reseland et al., "Inhibitor–Stimulated Non–Parallel Pancreatic Secretion in Man: Hormonal and Neural Regulation?," *Scan. J. Gastroenterol.*, 30: 72–80 (1994).

Reseland et al., "Proteinase Inhibitors Induce Selective Stimulation of Human Trypsin and Chymotrypsin Secretion[1,2]," *J. Nutr.*, 126: 634–642 (1996).

Saluja et al., "A Cholecystokinin–Releasing Factor Mediates Ethanol–Induced Stimulation of Rat Pancreatic Secretion," *J. Clin. Invest.*, 99(3): 506–512 (1997).

Schwartz et al., "Gastric Branch Vagotomy Blocks Nutrient and Cholecystokinin–Induced Suppression of Gastric Emptying," *Am. J. Physiol.*, 264: R630–637 (1993). (Abstract).

Slaff et al., "Protease–Specific Suppression of Pancreatic Exocrine Secretion," *Gastroenterology*, 87(1): 44–52 (1984). (Abstract).

Spannagel et al., "Purification and Characterization of a Luminal Cholecystokinin–Releasing Factor from Rat Intestinal Secretion," *Proc. Natl. Acad. Sci. USA*, 93: 4415–4420 (1996).

Spannagel et al., "An Amino–Terminal Fragment of LCRF, LCRF–(1–35), Has The Same Activity as the Natural Peptide," *Am. J. Physiol.*, 273: G754–758 (1997).

Spannagel et al., "Bioactivity of Intraduodenally and Intravenously Infused Fragments of Luminal Cholecystokinin Releasing Factor (LCRF)," *Regulatory Peptides*, 73: 161–164 (1998).

Spiegelman B. & Flier, J., "Adipogenesis and Obesity: Rounding Out the Big Picture," *Cell*, 87: 377–389 (1996).

Tarasova et al., "Distribution and Localization of a Novel Cholecystokinin–Releasing Factor in the Rat Gastrointestinal Tract," *Endrocrinology*, 138(12): 5550–5554 (1997).

The National Heart, Lung, and Blood Institute in cooperation with The National Institutes of Diabetes and Digestive and Kidney Diseases, "Clinical Guidelines on the Identification, Evaluation, and Treatment of Overweight and Obesity in Adults," NIH Publication No. 998–4083 (1998).

US Department of Health and Human Services, "Cardiac Valvulopathy Associated with Exposure to Fenfluramine or Dexfenfluramine: U.S. Department of Health and Human Services Interim Public Health Recommendations," *MMWR Morb. Mortal Wkly. Rep.*, 46(45): 1061–1066 (1997). (Abstract).

T. A. Wadden, "Treatment of Obesity by Moderate and Severe Caloric Restriction. Results of Clinical Research Trials," *Ann. Intern. Med.*, 1(119): 688–693 (1993). (Abstract).

International Search Report corresponding to PCT/US 00/33592; date of mailing: Dec. 12, 2001.

\* cited by examiner

FIGURE 1

| Oligomer Construction | |
|---|---|
| hydrophobic portion:<br>alkyl chain (2-22 carbon)<br>hydrophilic portion:<br>PEG<br>(2-5 kDa) | PEG oligomer or polymer<br><br>S1 — LCRF — Y35<br>C—N-H<br>COOH<br>Alkyl chain |
| Design 1<br>Branched polymer on N-term, non-hydrolyzable linkage, C-term and K19 un-conjugated | Polymer<br>Polymer — LCRF<br>S1 — K19 — Y35<br>COOH<br>Non-hydrolyzable bond |
| Design 2<br>Branched polymer on N-term, non-hydrolyzable linkage, K19 epsilon N conjugated to a linear polymer with a hydrolyzable linkage, C-term un-conjugated | Polymer<br>Polymer<br>LCRF — Hydrolyzable bond<br>S1 — K19 — Y35<br>COOH<br>Polymer<br>Non-hydrolyzable bond |
| Design 3<br>Linear polymer on N-term, Hydrolyzable linkage, K19 and K35 epsilon N and conjugated to a linear polymer with a hydrolyzable linkages.<br>Y35 → K35 mutation | Polymer — Polymer Hydrolyzable bonds Polymer<br>LCRF<br>S1 — K19 — K35 — COOH<br>Hydrolyzable bond |

SEQUENCE LISTING

<160> NUMBER OF SEQ ID NOS: 1

<210> SEQ ID NO 1
<211> LENGTH: 41
<212> TYPE: PRT
<213> ORGANISM: Homo sapiens

<400> SEQUENCE: 1

Ser Thr Phe Trp Ala Tyr Gln Pro Asp Gly Asp Asn Asp Pro Thr Asp
 1               5                  10                  15

Tyr Gln Lys Tyr Glu His Thr Ser Ser Pro Ser Gln Leu Leu Ala Pro
            20                  25                  30

Gly Asp Tyr Pro Cys Val Ile Glu Val
        35                  40

AMPHIPHILIC POLYMERS AND POLYPEPTIDE CONJUGATES COMPRISING SAME

BACKGROUND OF THE INVENTION

The present invention relates generally to a novel technology for conjugating amphiphilic oligomers and polymers to peptides in order to modulate their pharmacokinetic profile and thereby improve their clinical utility. The conjugates of the invention have the ability to stabilize and deliver luminal cholecystokinin releasing factor (LCRF) to receptors in the gut, without absorption in the bloodstream.

Endogenous LCRF acts at receptors on the luminal surface of gut epithelial cells, causing them to release cholecystokinin (CCK), a polypeptide hormone that induces satiety and reduces food intake, into the bloodstream. Exogenous LCRF, stabilized and delivered to the gut, will mimic normal physiological activity. The chemical modification of peptides regulating feeding behavior has the potential to treat obesity, a serious and growing public health problem in all industrialized nations, especially the United States.

Obesity is near epidemic proportions in industrialized countries, and its prevalence is increasing. The pathogenesis of obesity is complex, involving the interaction of lifestyle, dietary, behavorial and genetic factors. It is an object of the present invention to provide a drug that will induce satiety and will thereby produce weight loss.

The role of neuro- and gastric-peptides in regulation of feeding has been a major focus of obesity research. Convincing evidence exists that CCK inhibits feeding. (Schwartz, G. J., Berkow, G., McHugh, P. R., Moran, T. H., "Gastric Branch Vagotomy Blocks Nutrient and Cholecystokinin-induced Suppression of Gastric Emptying," Am. J. Physiol., 264:R630–7 (1993) (the disclosure of which is incorporated herein in its entirety)). Regulation of CCK expression is achieved in large part by regulation of LCRF, which is constitutively expressed in the duodenum in rats. In humans, it is postulated that stimulation by nutrients is required to stimulate secretion of the putative CCK-releasing factor. (Liddle, R. A. "Cholecystokinin Cells," Ann. Rev. Physiol., 59:221–42 (1997) (the disclosure of which is incorporated herein in its entirety)). After a protein meal, proteins in the food saturate the available trypsin, leaving a greater amount of LCRF unhydrolyzed, which then binds to the CCK cells. This causes them to release CCK, leading to satiety.

In one aspect, the conjugates of the present invention can be used to target the LCRF receptor with LCRF, its natural agonist, in order to initiate CCK release.

It is an object of the invention to provide a means for delivering LCRF to its target receptor. This object is achieved by conjugation of PEG oligomers or polymers modified with alkyl groups to proteins and peptides, to improve their pharmacologic properties. The present invention uses amphiphilic oligomer and polymer conjugation to vary the hydrophobicity and hydrophilicity of drug molecules. This reduces immunogenicity, prevents enzymatic degradation and facilitates oral delivery and partitioning to various tissues.

It is another object of the invention to provide conjugated LCRF which will be able to induce CCK release from CCK-releasing cells, leading to satiety and a reduction in food intake. We propose to deliver LCRF using our proprietary amphiphilic polymer conjugation technology, which will protect LCRF from proteolysis and confine it to the lumen of the gut for an extended period of time, producing satiety. We propose that such a conjugated LCRF would be an effective and safe therapeutic for chronic treatment of obesity.

The invention also provides synthetic methods for attaching an amphiphilic polymer to the N-terminal residues of LCRF, a 35 amino acid fragment that exhibits all the biological activity of full-length LCRF.

The amphiphilic conjugate comprises a polyethylene glycol (PEG) moiety and an alkyl chain. The alkyl chain can integrate into membranes on the epithelium of the intestine, bringing the conjugate in close proximity to LCRF receptors, which are located on the CCK-releasing cell surface. Stability of the peptide will be prolonged to maintain bioactivity. Moreover, where greater stability and a reduced tendency to penetrate the intestinal epithelium is required, peptides can be provided with conjugates at the N-terminus, at K19 and the C-terminus.

The operability of the LCRF conjugate molecules can be validated in a cell-based assay, using freshly prepared CCK-releasing cells obtained from rat intestine. A radioimmunoassay (RIA) can be used to detect CCK release.

LCRF is secreted in the duodenum and is physiologically regulated by proteolysis, particularly by trypsin. By protecting LCRF from proteolytic digestion, it will retain activity, bind to, and activate, LCRF receptors on CCK cells.

An amphiphilic polymer can be covalently attached to the ε amino group of $K19^1$, adjacent to the only trypsin cleavage site in LCRF (1–41), thus protecting LCRF from trypsin proteolysis by steric hindrance. It is preferable that modifications made to LCRF must not obstruct key residues involved in receptor binding. Since it is known that K19 is within the region crucial for receptor binding, it is preferable to attach the K19 conjugate with a linker that is slowly hydrolyzed under conditions found in the duodenum. As the K19 conjugate is released, the peptide then regains full activity. Slow hydrolysis may also extend action of the delivered LCRF, to minimize dosing.

About 55% of the US population is overweight or obese, with serious public health consequences. (The National Heart Lung and Blood Institute in cooperation with The National Institutes of Diabetes and Digestive and Kidney Diseases, "Clinical Guidelines on the Identification, Evaluation, and Treatment of Overweight and Obesity in Adults," NIH Publication no. 998-4083 (1998) (the disclosure of which is incorporated herein in its entirety)). Three of the most serious sequelae of obesity are heart disease, hypertension, and diabetes. Dieting and exercise have been largely unsuccessful long-term strategies for most overweight pepole (Wadden, T. A. "Treatment of Obesity by Moderate and Severe Caloric Restriction, Results of Clinical Research Trials," Ann. Intern. Med., 119:688–693 (1993) (the disclosure of which is incorporated herein in its entirety)); thus there is a need for pharmaceuticals that suppress appetite. One approach to appetite suppression is to induce release of CCK, a peptide hormone that produces satiety and reduces feeding.

CCK is one component of the hormonal system that tightly regulates hunger and satiety, digestion, and disposal of nutrients. CCK has several activities: it induces satiety and reduces food intake; stimulates gallbladder contraction; increases pancreatic enzyme secretion; and delays gastric emptying. When food, especially fat and protein, enters the small intestine, CCK is released into the blood where it binds to receptors in the peripheral nerves, pancreas, gall bladder, and stomach. (Mutt, V. "Secretin and Cholecystokinin," in "Gastrointestinal Hormones," 251–320 (ed. V. Mutt, San Diego, Academic Press, 1998) (the disclosure of which is incorporated herein in its entirety)).

Figure 1:
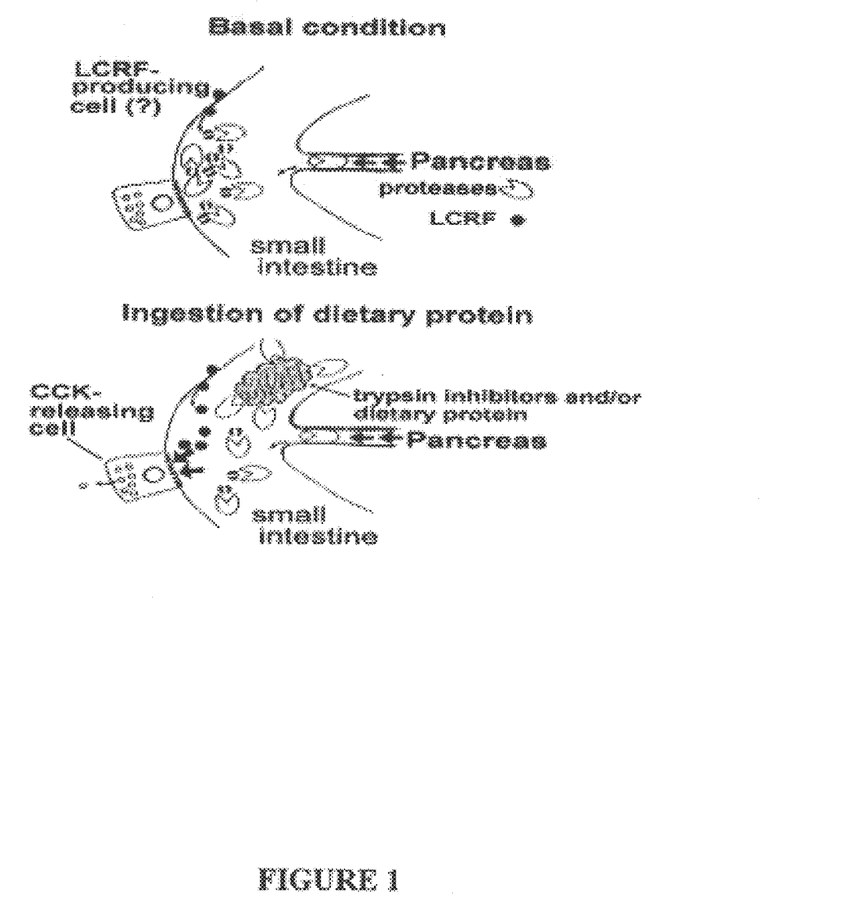
FIG. 1 summarizes the regulation of CCK release by LCRF.

CCK release in the intestine is under negative feedback regulation. (Green, G. M. & Lyman, R. L. "Feedback Regulation of Pancreatic Enzyme Secretion as a Mechanism for Trypsin Inhibitor-induced Hypersecretion in Rats," *Proc. Soc. Exp. Biol. Med.*, 140:6–12 (1972) (the disclosure of which is incorporated herein in its entirety)). LCRF is a constitutively produced, trypsin-sensitive intestinal CCK-releasing peptide responsible, in part, for this negative feedback phenomenon. (Lu, L., Louje, D., & Owyang, C. "A Cholecystokinin Releasing Peptide Mediates Feedback Regulation of Pancreatic Secretion," *Am. J. Physiol.*, 256:G430–G435 (1989); Miyasaka, K., Guan, D., Liddle, R. A. & Green, G. M. "Feedback Regulation by Trypsin: Evidence for Intraluminal CCK-releasing Peptide, *Am. J. Physiol.*, 257:G175–G181 (1989) (the disclosure of which is incorporated herein in its entirety)). FIG. 1 (adapted from Miyasaka K & Funakoshi A (1998) Pancreas 16:279) summarizes the regulation of CCK release by LCRF. In the basal or fasting state, all LCRF is rapdily cleaved by trypsin. Upon ingestion of protein or trpysin inhibitors, some LCRF remains intact and binds to the CCK-releasing cell, causing CCK release and satiety. When LCDF is infused into the duodenum of rats with trypsin inhibitors, it causes a reduction of food intake. (Green, G. M., Taguchi, S., Friestman, J., Chey, W. Y., Liddle, R. A. "Plasma Secretin, CCK, and Pancreatic Secretion in Response to Dietary Fat in the Rat," *Am. J. Physiol.*, 256:G1016–1021 (1989) (the disclosure of which is incorporated herein in its entirety)).

LCRF is a Potent CCK Releasing Factor. LCRF is one of at least three peptides responsible for causing CCK cells to release CCK into the bloodstream. LCRF is the most potent of these peptides. Two other peptides secreted into the intestines are also found to stimulate CCK release: diazepan binding inhibitor and monitor peptide. The latter controls CCK release by positive feedback regulation. However, the potency of these two peptides for stimulating CCK release is less than LCRF (down 100–1,000 fold and 6 fold respectively). (Liddle, R. A., unpublished results; H. Spannagel A. W., Reeve, J. R., Liddle, R. A., Guan, D., Green, G. M. "An Amino-terminal Fragment of LCRF, LCRF (1–35), Has the Same Activity as the Natural Peptide," *Am. J. Physiol.*, 273:G754–758 (1997) (the disclosures of which are incorporated herein in their entireties)).

The nature of the receptor-LCRF interaction has not been established, as the receptor has not been identified. However, there is strong evidence that the receptor resides on the cell surface. Dr. Rodger Liddle of Duke University, our collaborator, has demonstrated that LCRF stimulates CCK release from intestinal endocrine cells through a calcium influx pathway. (Liddle, R. A., Prpic, V., Wang, Y., Romac, J., Green, G. M., Reeve, J. R. "Luminal Cholecystokinin Releasing Factor (LCRF) Stimulated CCK Release from Intestinal Endocrine Cells through a Calcium Influx Pathway," *Gastroenterology*, 116:A622 (1999) (the disclosure of which is incorporated herein in its entirety)). Increase in intracellular calcium are a typical signaling mechanism for receptor signaling and strongly suggest that the receptor resides on the cell surface.

Feeding of trypsin inhibitors or diversion of bile-pancreatic juice stimulates pancreatic exocrine secretion and CCK release in rats and humans. (Slaff, J. D., Jacobson, C. R., Tulman, C., et al., "Protease-specific Suppression of Pancreatic Exocrine Secretion," *Gastroenterology*, 87:44–52 (1984) (the disclosure of which is incorporated herein in its entirety)). A CCK-stimulating peptide that is sensitive to tryptic digestion was first purified from rat intestinal washings. (Spannagel, A. W., Green, G. M., Guan, D., Liddle, R. A., Faull, K. & Reeve, J. R. "Purification and Characterization of a Luminal Cholecystokinin-releasing Factor from Rat Intestinal Secretion, *Proc. Natl. Acad. Sci. USA*, 93:4415–4420 (1996) (the disclosure of which is incorporated herein in its entirety)). This peptide, named luminal cholecystokinin releasing factor (LCRF), stimulates CCK release from isolated rat, mouse, and human intestinal cells and a cell line derived from an intestinal endocrine tumor (STC-1 cells). (Rindi, G. S., Grant, S. G. N., Yiangou, Y., et al. "Development of Neuroendocrine Tumors in the Gastrointestinal Tract of Transgenic Mice. Heterogeneity of Hormone Expression," *Am. J. Pathol.*, 136:1349–1363 (1990) (the disclosure of which is incorporated herein in its entirety)). The 35 residue N-terminal fragment of LCRF has all of the biological activity of the native peptide, which is between 60–65 residues long (8136 Da). Using synthetic peptides, it has been found that residues 11–25 are responsible for the CCK releasing properties of LCRF, producing about 60% of the activity of the 1–41 fragment. (Spannagel, A. W., Reeve, J. R., Jr, Greeley, G. H., Jr, Yanaihara, N., Liddle, R. A., Green, G. M. "Bioactivity of Intraduodenally and Intravenously Infused Fragments of Luminal Cholecystokinin Releasing Factor (LCRF)," *Regulatory Peptides*, 73:161–4 (1998) (the disclosure of which is incorporated herein in its entirety)). However, the gene for LCRF has not been identified, and as of December 1999, no homologues exist in publicly available protein or DNA sequence databases.

The present invention provides an LCRF conjugate that retains the capacity to bind to the LCRF receptor on CCK cells; is protected from proteolytic cleavage; and is confined to the lumen of the gut by virtue of its molecular weight. LCRF receptor binding will cause the CCK cells to release CCK into the blood stream, leading to satiety and a reduction in food intake. Accordingly, the present invention provides LCRF conjugates that provide an effective orally delivered treatment of obesity.

Practical limitations exist to the use of peptides as drugs. Proteolysis, both in the gut and in the bloodstream, is a major barrier to using peptides as therapeutics. Indeed, the transient nature of many endogenous peptides, including LCRF, is a feature of their regulatory function. Another difficulty encountered with non-endogenous peptides is immunogenicity. As a result of these problems, the approach of the pharmaceutical industry has been to create small, non-peptide molecules using medicinal chemistry. And while medicinal chemistry has been successful, it is very time consuming. Furthermore, chemical drugs may have unexpected toxicity or teratogenicity.

While the use of "PEGylated" proteins is well established, to date they have been confined to injectable use. The present invention provides orally available conjugates of polypeptides, such as insulin, leu-enkephalin, and calcitonin. (Ekwuribe, N., Ramaswamy, M., Allaudeen, H. S., Rajagopalan, J. S., et al., "Oral Insulin Delivery: Hydrolyzable Amphiphilic Oligomer Conjugates Prolong Glucose Reduction," *Proceed Intl. Symp. Control Release Bioactiv. Materials,"* Abstract 242 (1999); Anderson, W. R., Ekwuribe, N., Ansari, A., Harris, T. M., Surguladze, D. "Structure Activity Relationship Assessment of Conjugated Enkephalins in Centrally Mediated Analgesia," *Soc. for Neuroscience*, Abstracts 25(1):180 (1999); Krishnan, D. R., Ramaswamy, M., Rajagopalan, J. S., Anderson, W. R., Allaudeen, H. S., Myung, S., Ekwuribe, N. "Oral Delivery of Calcitonin by Conjugation with Amphiphilic Oligomers," *Proceed. Intl. Symp. Control Release Bioactiv. Materials,* Abstract 243(1999) (the disclosures of each of which are incorporated herein in their entireties)). Specifically, present invention provides conjugates comprising PEG units linked to alkyl chains. (U.S. Pat. No. 5,681,811: Conjugation-stabilized Therapeutic Agent Compositions, Delivery and Diagnostic Formulations Comprising Same, and Method of Making and Using the Same (the disclosure of which is incorporated herein in its entirety)). By adjusting the number of PEG monomers, the type and length of the alkyl chain and the exact nature of the PEG-peptide linkage, desired properties of lipophilicity can be tailored to a specific use. In addition, the exact nature of the PEG-peptide linkage can be varied such that it is stable or sensitive to hydrolysis at physiological pH. The hydrolyzable linker allows the intact, unconjugated peptide to be released over time, to act as a prodrug.

Cell-based assays can be used to validate to capacity of amphiphilic oligomer-LCRF conjugates for oral delivery in animals. Animal studies can then be used to validate the appetite-suppressing ability of the conjugates. For example, rats can be subjected to behavioral studies to assess the appetite suppression profile of the LCRF-conjugate. If the conjugate shows desired ability to suppress appetite in rats, the compound will be subjected to detailed pharmacokinetic, and pharmacodynamic studies in rats, as well as toxicity testing.

An enormous effort is being made to develop pharmaceuticals for the treatment of obesity. A recently approved drug for obesity is the lipase inhibitor orlistat, which prevents fat uptake, but does not affect appetite. Orlistat (Xenical) may lead to diminished fat-soluble vitamin intake and can have very unpleasant side effects. Marketed appetite suppressants include sibutramine (Meridia), a mixed neurotransmitter reuptake inhibitor, and sympathomimetic agents. However, use of these drugs is limited by CNS effects. In 1997, the appetite suppressant drug combination fenfluramine and dexfenfluramine (Fen-Phen) was found to cause cardiac valvulopathy and was withdrawn from the market. (U.S. Department of Health and Human Services, "Cardiac Vavulopathy Associated with Exposure to Fenfluramine and Dexfenfluramine: U.S. Department of Health and Human Services Interim Public Health Recommendations," *Morb. Mortal. Wkly. Rep.,* 46:1061–1066 (1997) (the disclosure of which is incorporated herein in its entirety)). Neuropeptide Y antagonists, kappa opioid receptor antagonists, melanocortin-4 agonists and beta-3 adrenergic receptor antagonists are all in preclinical development for appetite suppression. Leptin and neuropeptide Y, two endogenous peptides, are involved in controlling the long-term regulation of food consumption and energy expensiture. (Friedman, J. M. Halaas, J. L. "Leptin and the Regulation of Body Weight in Animals," *Nature,* 395:763–770 (1998) (the disclosure of which is incorporated herein in its entirety)). While these two peptides are being studied intensely, neither has proven successful in clinical studies.

The CCK pathway is involved in the modulation of feeding patterns, rather than long-term weight maintenance. (Spiegelman, B. M., Flier, J. S. "Adipogenesis and Obesity: Rounding Out the Big Picture," *Cell,* 87:377–389 (1996) (the disclosure of which is incorporated herein in its entirety)). Three of the approaches to discovery and development of drugs for obesity directly target the CCK pathway, including CCK-A agaonists, inhibitors of CCK proteolysis, and agonists to the LCRF receptor.

Several benzodiazepine analogs and peptidomimetics are in preclinical development as CCK-A agonists. These compounds have been shown to decrease food intake in rats and are in preclinical development for the treatment of obesity by Abbott Laboratories and Glaxo Wellcome. Further validation of this approach is the use of CCK-A antagonists as a treatment for anorexia nervosa.

Butabindide is a cholecystokinin-inactivating peptidase inhibitor that is undergoing preclinical investigation by INSERM, France, for the treatment of obesity. However, the duration of action of butabindide is too brief for clinical utility, and investigation of other analogs is underway.

Synthetic small molecules that are LCRF receptor against could be used to stimulate CCK release. However, structure-based drug design is not a currently viable strategy because of lack of structural data on either LCRF or its receptor.

By 2005, the number of people dieting to lose weight for health reasons is expected to be 5.8 million. The total market for weight-loss products and services, including diet foods, in the United States for health or cosmetic reasons is about $30 billion. Despite the paucity of safe and effective products, Americans spent $243 million on obesity drugs in 1998. Clearly, the market for a safe, effective and chronic treatment for obesity is tremendous.

SUMMARY OF THE INVENTION

The present invention provides a composition comprising a protein or peptide, such as LCRF, coupled with one or more molecules of a non-naturally-occurring polymer, said polymer comprising a lipophilic moiety and a hydrophilic polymer moiety, thereby imparting balanced lipolhilic and hydrophilic characteristics to the composition such that the composition is soluble in pharmaceutically acceptable solvents and able to interact with biological membranes.

The present invention provides a composition comprising a protein or peptide, such as LCRF, coupled with one or more molecules of a non-naturally-occurring polymer, said polymer comprising: (i) a lipophilic moiety; and (ii) a hydrophilic polymer moiety, thereby imparting balanced lipolhilic and hydrophilic characteristics to the conjugate such that the conjugate is soluble in pharmaceutically acceptable solvents and able to interact with biological membranes.

The present invention provides a composition comprising a protein or peptide, such as LCRF, coupled with one or more molecules of a non-naturally occurring polymer comprising a lipophilic moiety and a hydrophilic moiety wherein the composition is soluble in aqueous solvents and the LCRF is active in prophylaxis or treatment of obesity.

The present invention provides a composition comprising a protein or peptide, such as LCRF, covalently coupled with one or more molecules of a polymer comprising (i) a linear polyalkylene glycol moiety and (ii) a lipophilic moiety, wherein the physiologically active peptide, the linear polyalkylene glycol moiety and the lipophilic moiety are conformationally arranged in relation to one another such that the LCRF in the LCRFcomposition has an enhance in vivo resistance to enzymatic degradation, relative to the LCRFalone.

The present invention provides a composition comprising a triglyceride backbone moiety, having: LCRF covalently coupled with the triglyceride backbone moiety through a polyalkylene glycol spacer group bonded at a carbon atom of the triglyceride backbone moiety; and at least one fatty acid moiety covalently attached either directly to a carbon atom of the triglyceride backbone moiety or covalently joined through a polyalkylene glycol spacer moiety.

The present invention provides polysorbate complex comprising a polysorbate moiety including a triglyceride backbone having a fatty acid group covalently coupled to one of the α,α' and β carbon atoms thereof, and having a polyethylene glycol group covalently coupled to one of the α,α' and β carbon atoms thereof.

The present invention provides a stable, aqueously soluble, conjugated LCRF complex comprising a LCRF stabilizingly and conjugatively coupled to a polyethylene glycol modified glycolipid moiety.

The present invention provides a polysorbate complex comprising a polysorbate moiety including a triglyceride backbone having covalently coupled to carbon atoms independently selected from α,α' and β carbon atoms thereof, functionalizing groups including a fatty acid group; and a polyethylene glycol group having a physiologically active moiety covalently bonded thereto.

The present invention also provides an oral administration dosage form for the treatment of obesity, comprising a pharmaceutically acceptable carrier and a stable, aqueously soluble, conjugated LCRF complex comprising LCRF coupled to a physiologically compatible polyethylene glycol modified glycolipid moiety.

The present invention also provides a method of treating obesity in a human or non-human mammalian subject exhibiting such deficiency, comprising orally administering to the subject an effective amount of a conjugated LCRF composition comprising a stable, aqueously soluble, conjugated LCRF complex comprising LCRF covalently coupled to a physiologically compatible polyethylene glycol modified glycolipid moiety.

The present invention provides a method of prophylactically or interventionally treating potential or developed obesity in a human or non-human mammalian subject LCRF, comprising administering to the subject an effective amount of a conjugated LCRF composition comprising a stable, aqueously soluble, conjugated LCRF complex comprising LCRF coupled to a physiologically compatible polyethylene glycol modified glycolipid moiety.

The present invention provides a method of prolonging the activity of LCRF in an in vivo or in vitro system, comprising conjugatively coupling LCRF with one or more molecules of a non-naturally-occurring polymer comprising a lipophilic moiety and a hydrophilic polymer moiety to yield a conjugatively coupled polymer-LCRF composition, and introducing the conjugatively coupled polymer-LCRF composition to the in vivo or in vitro system.

The present invention also provides, in a preferred embodiment, a compound of the formula:

where n is from 3 to 230 and m is from 0 to 20.

The present invention also provides, in a preferred embodiment, a compound of the formula:

where n is from 3 to 230 and m is from 0 to 20 and X is selected from the group consisting of N, O or S.

The present invention also provides, in a preferred embodiment, a compound of the formula:

where n is from 3 to 230 and m is from 0 to 20, where the protein is preferably a therapeutic protein.

The present invention also provides, in a preferred embodiment, a compound of the formula:

where n is from 3 to 230 and m is from 0 to 20 and X is selected from the group consisting of N, O or S, where the protein is preferably a therapeutic protein.

DETAILED DESCRIPTION OF THE INVENTION

While the ensuing description is primarily and illustratively directed to the use of LCRF as a peptide component in various compositions and formulations of the invention, it will be appreciated that the utility of the invention is not thus limited, but rather extends to any peptide species which are covalently or associatively conjugatable in the manner of the invention, including, but not limited to, the following peptide species: calcitonin, ACTH, glucagon, somatostain, somatotropin, somatomedin, parathyroid hormone, erythropoietin, hypothalmic releasing factors, prolactin, thyroid stimulating hormone, endorphins, antibodies, hemoglobin, soluble CD-4, clotting factors, tissue plasminogen activator, enkephalins, vasopressin, non-naturally occurring opioids, superoxide dismutase, interferon, asparaginase, arginase, arginine deaminease, adenosine deaminase ribonuclease, trypsn, chemotrypsin, and papain, alkaline phosphatase, and other suitable enzymes, hormones, proteins, polypeptides, enzyme-protein conjugates, antibody-hapten conjugates, viral epitopes, etc.

The disclosures of the following U.S. patent applications are incorporated herein by reference: Ser. Nos. 08/059,701; 08/276,890; 08/509,422; 08/958,383; 09/134,803; 09/336,548; 09/429,798; 60/153,579; 60/153,649; 60/160,412; 60/161,864; 60/161,884. The disclosure of International Patent Application No. PCT/US99/18248 is incorporated herein by reference.

One objective of the present invention is to provide suitable polymers for conjugation with peptides so as to obtain the desirable characteristics enumerated above. Another objective is to utilize such modified peptides for sustained in vivo delivery of the peptide. Yet another objective is to use the technology to deliver peptides orally in their active form.

A further objective is to employ associatively conjugated peptides for use in immunoassay, diagnostic, and other non-therapeutic (e.g., in vitro) applications. Still another objective of the present invention is to provide stabilizingly conjugated peptide compositions, including covalently bonded compositions variously suitable for in vivo as well as non-in vivo applications, and to alternatively provide non-covalent, associatively conjugated peptide compositions variously suitable for in vivo as well as non-in vivo applications.

Within the broad scope of the present invention, a single polymer molecule may be employed for conjugation with a plurality of peptide species, and it may also be advantageous in the broad practice of the invention to utilize a variety of polymers as conjugating agents for a given peptide; combinations of such approaches may also be employed. Further, stabilizingly conjugated peptide compositions may find utility in both in vivo as well as non-in vivo applications. Additionally, it will be recognized that the conjugating polymer(s) may utilize any other groups, moieties, or other conjugated species, as appropriate to the end use application. By way of example, it may be useful in some applications to covalently bond to the polymer a functional moiety imparting UV-degradation resistance, or antioxidation, or other properties or characteristics to the polymer. As a further example, it may be advantageous in some applications to functionalize the polymer to render same reactive or cross-linkable in character, to enhance various properties or characteristics of the overall conjugated material. Accordingly, the polymer may contain any functionality, repeating groups, linkages, or other constituent structures which do not preclude the efficacy of the conjugated composition for its intended purpose. Other objectives and advantages of the present invention will be more fully apparent from the ensuing disclosure and appended claims.

Illustrative polymers that may usefully be employed achieve these desirable characteristics are described herein below in an exemplary reaction scheme. In covalently bonded peptide applications, the polymers may be functionalized and then coupled to free amino acid(s) of the peptide (s) to form labile bonds which permit retention of activity with the labile bonds intact. Removal of the bond by chemical hydrolysis and proteolysis then enhances the peptidal activity.

The polymers utilized in the invention may suitably incorporate in their molecules constituents such as edible fatty acids (lipophilic end), polyethylene glycol (water soluble end), acceptable sugar moieties (receptor interacting end), and spacers for peptide attachment. Among the polymers of choice, polysorbates are particularly preferred and are chosen to illustrate various embodiments of the invention in the ensuing discussion herein. The scope of this invention is of course not limited to polysorbates, and various other polymers incorporating above-described moieties may usefully be employed in the broad practice of this invention. Sometimes it may be desirable to eliminate one of such moieties and to retain others in the polymer structure, without loss of objectives. When it is desirable to do so, the preferred moieties to eliminate without losing the objectives and benefits of the invention are the sugar and/or the spacer moieties.

It is preferred to operate with polymers whose molecular weights fall between 100 and 10,000 daltons.

In the practice of the present invention, polyalkylene glycol residues of $C_2$–$C_4$ alkyl polyalkylene glycols, preferably polyethylene glycol (PEG), are advantageously incorporated in the polymer systems of interest.

The presence of these PEG residues will impart hydrophilic properties to the polymer and to the corresponding polymer-peptide conjugates. Certain glycolipids are known to stabilize proteins and peptides. The mechanism of this stabilization probably involves association of the glycolipid fatty acid moieties with the hydrophobic domain of the peptide or protein; aggregation of the protein or peptide is thus prevented. It also is known that aggregated peptides are poorly absorbed in the small intestine compared to native peptides. The invention therefore contemplates polymer-peptides products in which the peptides, e.g., LCRF, is conjugated with either the hydrophilic or hydrophobic residue of the polymer. The fatty acid portion of the polymer is provided to associate with the hydrophobic domain of the peptide and thus prevent aggregation in solution. The resulting polymer-peptide conjugates thus will be: stabilized (to chemical and enzymatic hydrolysis); water-soluble, due to the PEG residue; and, by virtue of the fatty acid-hydrophobic domain interactions, not prone to aggregation.

Polyalkylene glycol derivatization has a number of advantageous properties in the formulation of polymer-peptide conjugates in the practice of the present invention, as associated with the following properties of polyalkylene glycol derivatives: improvement of aqueous solubility, while at the same time eliciting no antigenic or immunogenic response; high degrees of biocompatibility; absence of in vivo biodegradation of the polyalkylene glycol derivatives; and ease of excretion by living organisms.

The polymers employed in the practice of the present invention thus comprise lipophilic and hydrophilic moieties, rendering the resulting polymer-peptide conjugate highly effective (bioactive) in oral as well as parenteral and other modes of physiological administration, and highly effective in non-physiological applications.

Set out below as illustrative examples of polymer-peptide conjugates of the present invention are the formulae of covalently bonded conjugates denoted for ease of subsequent reference as Conjugate 1, Conjugate 2, and Conjugate 3, and specific values of m, n, w, x, and y will be described in the ensuing discussion.

Conjugate 1:

wherein:
w + x + y + z = 20; and
R = oleic acid:

R = oleic acid: $CH_3(CH_2)_7CH\!\!=\!\!CH(CH_2)_7\overset{O}{\overset{\|}{C}}\!\!-\!\!$ Conjugate 2:

Conjugate 3:

Conjugate 1 features commercially available polysorbate monooleate at the center of the polymeric system, a sugar derivative used in many pharmaceutical applications. Lipophilic and absorption enhancing properties are imparted by the oleic acid chain, while the polyethylene glycol (PEG)

residues provide a hydrophilic (hydrogen bonding accepting) environment. LCRF is attached through a carbamate linkage adjacent to the PEG region of the polymer.

In Conjugate 2 the sugar residue is excluded, but LCRF is once again attached to the polymer through a carbamate bond adjacent to the hydrophilic PEG region of the polymer. The lipophilic fatty acid region of the polymer is thus some distance from the point of attachment to LCRF.

The arrangement described above for Conjugate 2 is reversed in the case of Conjugate 3. Once more the sugar residue is excluded, but in this structure the lipophilic fatty acid residue is closest to the point of attachment to LCRF and the hydrophilic PEG region is distant from the point of attachment, which is again through a carbamate bond.

In the general practice of the invention, various methods of coupling the polymers to the peptide are available and are discussed more fully hereinafter. In working with proteins and polypeptides, it should be realized that certain residue groups in the peptide are important in their overall biological integrity. It is important to choose a suitable coupling agent that does not unduly interfere with such residues. In some instances, it may be difficult to avoid coupling and therefore masking the activity of these important residues, but some activity may be traded for increased stability while maintaining the endowed beneficial properties. In in vivo applications, for example, frequency of dosing may thus be reduced, resulting in reduced costs and increased patient compliance.

The polymers utilized in protein/peptide conjugation in accordance with the invention are designed to incorporate good physical characteristics that enable them to achieve the desired objectives. Absorption enhancers, while enabling penetration of peptides through the cell membrane, do not improve the stability characteristics of the peptides, and in vivo applications may therefore utilize the polymer-peptide conjugates of the invention in formulations devoid of such penetration enhancers. One aspect of the present invention therefore relates to the incorporation of fatty acid derivatives within the polymer, to mimic penetration enhancers.

In the covalently conjugated polymer-peptide conjugates of the present invention, the peptide may be covalently attached to the water-soluble polymer by means of a labile chemical bond. This covalent bond between the peptide and the polymer may be cleaved by chemical or enzymatic reaction. The polymer-peptide product retains an acceptable amount of activity; full activity of the component peptide is realized when the polymer is completely cleaved from the peptide. Concurrently, portions of polyethylene glycol are present in the conjugating polymer to endow the polymer-peptide with high aqueous solubility and prolonged blood circulation capability. Glycolipids are usefully associated with the polymer in such a way that their fatty acid moieties occupy the hydrophobic domain of the peptide and thus prevent aggregation. Aggregation of peptides results in their being poorly absorbed in the small intestine. Unaggregated peptides are more easily absorbed by the small intestine. The incorporation of glycolipids into the conjugating polymer thus serves the purposes of improving stability and preventing peptide aggregation after conjugation. The modifications described above confer improved solubility, stability, and membrane affinity properties on the peptide. As a result of these improved characteristics the invention contemplates parenteral and oral delivery of both the active polymer-peptide species and, following hydrolytic cleavage, bioavailability of the peptide per se, in vivo applications.

The polymers used in the embodiment described below can be classified as polyethylene glycol modified glycolipids and plyethylene glycol modified fatty acids. Among preferred conjugating polymers may be mentioned polysorbates comprising monopalmitate, dipalmitate, tripalmitate, monolaurate, dilaurate, trialaurate, monooleate, dioleate, trioleate, monostearate, distearate, and tristearate. The number average molecular weight of polymer resulting from each combination is preferred to be in the range of from about 500 to about 10,000 daltons. Alternative polymers of preference for this embodiment are polyethylene glycol ethers or esters of fatty acids, such fatty acids being lauric, palmitic, oleic, and stearic acids, and the polymers ranging from 500 to 10,000 daltons in number average molecular weight. It is preferred to have a derivatizable group in the polymer, where such group can be at the end terminating with polyethylene glycol or at the end terminating with fatty acid. The derivatizable group may also be situated within the polymer and thus may serve as a spacer between the peptide and the polymer.

Several methods of modifying fatty acid sorbitan to achieve the desired polymer will be discussed in further detail with structural illustrations. Polysorbates are esters of sorbitols and their anhydrides, which are copolymerized with approximately twenty moles of ethylene oxide for each mole of sorbitol and sorbitol anhydrides. Shown below is the structure of a representative polymer.

(Formula 1)

The sum of w, x, y, z is 20 and $R_1$, $R_2$ and $R_3$ are each independently selected from the group consisting of lauric, oleic, palmitic and stearic acid radicals, or $R_1$ and $R_2$ are each hydroxyl while $R_3$ is lauric, palmitic, oleic or stearic acid radical. These polymers are commercially available and are used in pharmaceutical formulations. Where a higher molecular weight polymer is desired, it may be synthesized from glycolipids such as sorbitan monolaurate, sorbitan monooleate, sorbitan monopalmitate or sorbitan monostearate, and an appropriate polyethylene glycol. Structures of glycolipids which may be used as starting reagents are depicted below.

(Formula 1)

m = 10 to 16

In the synthesis of glycolipid polymers substituted in three positions with polyethylene glycol, a desired plyethylene glycol having two free hydroxyls at the termini is protected at one terminus with a trityl group in pyridine using one mole of trityl chloride. The remaining free hydroxyl group of the polyethylene glycol is converted to either tosylate or bromide. The desired glycolipid is dissolved in a suitable inert solvent and treated with sodium hydride. The tosylate or bromide of the protected polyethylene glycol is dissolved in inert solvent and added in excess to the solution of glycolipid. The product is treated with a solution of para-toluenesulfonic acid in anhydrous inert solvent at room temperature and purified by column chromatography. The structures of the transformation are depicted below.

(Formula 3)

m = 10 to 16
Sum of x, y, z = 8 to 240

By adjusting the molar equivalent of reagents and using the appropriate molecular weight range of polyethylene glycol, mono or disubstituted glycolipids of the desired molecular weight range can be obtained by following the above procedures.

(Formula 4)

wherein each n and m may vary independently, and have any suitable value appropriate to the specific peptide being stabilized, e.g., from 1 to 16.

The sugar portion of the glycolipid described above can be substituted with glycerol or aminoglycerol whose structural formulae are shown below.

(Formula 5)

-continued

In this modification, the primary alcohol is first etherified or esterified with a fatty acid moiety such as lauric, oleic, palmitic or stearic; the amino group is derivatized with fatty acids to form amides or secondary amino groups, as shown below.

(Formula 6)

wherein m may have any suitable value, e.g., from 10 to 16.

The remaining primary alcohol group is protected with a trityl group while the secondary alcohol group is converted with polyethylene glycol to a desired polymer. Usually, the polyethylene glycol bears a leaving group at one terminal and a methoxy group at the other terminal. The polyethylene glycol is dissolved in inert solvent and added to a solution containing glycolipid and sodium hydride. The product is deprotected in para-toluenesulfonic acid at room temperature to give the desired polymer as depicted.

(Formula 7)

p-TsA = Para toluenesulfonic acid

Sometimes it is desirable to incorporate fatty acid derivatives in different parts of the polyethylene glycol chain to achieve certain physicochemical properties similar to polysorbates that have been substituted with two/three molecules of fatty acids, e.g., polysorbates trioleate.

Structures representing the polymers are shown in the reaction scheme below as the open chain of the polysorbate.

A

B

↓

C

↓

D

Pr = Peptides, Proteins, Protein Drugs;
R = Alkyl, $C_5$ to $C_{18}$;
n = 5 to 120;

$$X = O, S, \overset{O}{\underset{\|}{C}}-O-, \overset{O}{\underset{\|}{C}}-NH-; \quad PrNH-\overset{O}{\underset{\|}{C}}-O:$$

$$NH-\overset{O}{\underset{\|}{C}}-O-\ \text{could be}\ -\overset{O}{\underset{\|}{C}}-O-,\ HN-\overset{O}{\underset{\|}{C}}-;$$

E

↓

F

↑

G

Pr = Peptides, Proteins, Protein Drugs;
R = Alkyl, $C_5$ to $C_{18}$;
n = 5 to 120;
m = 2 to 15;

$$X = O, S, \overset{O}{\underset{\|}{C}}-O-, \overset{O}{\underset{\|}{C}}-NH-; \quad NH-\overset{O}{\underset{\|}{C}}-O:$$

$$-NH-\overset{O}{\underset{\|}{C}}-O-\ \text{could be}\ -\overset{O}{\underset{\|}{C}}-O-,\ HN-\overset{O}{\underset{\|}{C}}-;$$

(Formulae 8)

H

Pr = Peptides, Proteins, Protein Drugs;
R = Alkyl, $C_5$ to $C_{18}$;
m = 5 to 18;
n = 2 to 15;
y = 5 to 120;
and wherein m, n, and y may be independently varied within the above, ranges, relative to one another.

In the synthesis of polymer A, it is desirable to protect the hydroxyl moieties on the first and second carbon of glycerol, e.g. solketal. The remaining hydroxyl group is converted to the sodium salt in an inert solvent and reacted with halogenated or tosylated polyethylene glycol in which one end of the polyethylene glycol has been protected as an ester. The glycerol protection is removed and the resulting two free hydroxyl groups are converted to the corresponding sodium salts. These salts are reacted in inert solvent with polyethylene glycol which has been partially derivatized with fatty acids. Reaction takes place after the free hydroxyl is converted to the tosylate or bromide.

Polymer G is synthesized in the same manner except that the protected glycol is first reacted with esters of fatty acids which have been halogenated at the terminal carbon of the acid.

In the synthesis of polymer C, it is preferable to start with 1, 3-dihalo-2-propanol. The dihalo compound is dissolved in inert solvent and treated with the sodium salt of two moles of polyethylene glycol which has been previously derivatized with one mole of a fatty acid moiety. The product is purified by chromatography or dialysis. The resulting dry product is treated, in inert solvent, with sodium hydride. The sodium salt thus formed is reacted with a halo derivative of partially protected polyethylene glycol.

Sometimes it may be desired to omit the sugar portion of the polymer. The resulting polymer still contains a polyethylene glycol fragment. The membrane affinity properties of the fatty acid moiety may be retained by substituting a fatty acid proper with a lipophilic long chain alkane; biocompatibility is thus preserved. In one instance of this embodiment the polyethylene glycol with two terminal free hydroxyl groups is treated with sodium hydride in inert solvent. One equivalent weight of a primary bromide derivative of a fatty acid-like moiety is added to the polyethylene glycol solvent mixture. The desired product is extracted in inert solvent and purified by column chromatography if necessary.

(Formula 9)

Where it is desired to form an ester linkage between the fatty acid and the polyethylene glycol, the acid chloride of the acid is treated with excess of desired polyethylene glycol in suitable inert solvent. The polymer is extracted in inert solvent and further purified by chromatography if necessary.

(Formula 10)

In some modifications of peptides, it is desired to conjugate the fatty acid moiety directly to the peptide. In this case the polymer is synthesized with the derivatizable function placed on the fatty acid moiety. A solution of monomethoxypolyethylene glycol of appropriate molecular weight in inert solvent is treated with sodium hydride followed by the addition of solution containing the ethyl ester of a fatty acid bearing a leaving group at the terminal carbon of the acid. The product is purified after solvent extraction and if necessary, by column chromatography.

(Formula 11)

The ester protection is removed by treating with dilute acid or base.

(Formula 12)

Where it is desired to form a carbamate bond with the polypeptide, the carboxyl or ester is converted to a hydroxyl group by a chemical reduction method known in the art.

(Formula 13)

The functional groups that are used in polypeptide conjugation are usually at a terminal end of the polymer, but in some cases, it is preferred that the functional group is positioned within the polymer. In this situation, the derivatizing groups serve as spacers. In one instance of this embodiment, a fatty acid moiety may be brominated at the carbon alpha to the carboxylic group and the acid moiety is esterified. The experimental procedure for such type of compound is similar to the one outlined above, resulting in the product shown below.

(Formula 14)

When an extended spacer is desired, a polyethylene glycol monoether may be converted to an amino group and treated with succinic anhydride that has been derivatized with a fatty acid moiety. A desired polyethylene glycol bearing primary amine is dissolved in sodium phosphate buffer at pH 8.8 and treated with a substituted succinic anhydride fatty acid moiety as shown in the scheme below. The product is isolated by solvent extraction and purified by column chromatography if necessary.

(Formula 15)

It is to be understood that the above reaction schemes are provided for the purposes of illustration only and are not to be limitingly construed in respect of the reactions and structures which may be beneficially utilized in the modification of peptides in the broad practice of the present invention, e.g., to achieve solubility, stabilization, and cell membrane affinity for parenteral and oral administration.

The present invention provides conjugates of biocompatible polymers with as biologically active macromolecules, diagnostic reagents, etc., which may for example consist of peptides, proteins, enzymes, growth hormones, growth factors and the like. Such macromolecular compounds may be built with alpha-amino acids joined in an amide linkage to form peptide oligomers and polymers. Depending on the functions of these substances, the peptide components can be proteins, enzymes, growth hormones, etc. For the purpose of brevity, these substances are collectively referred to here as peptides and are designated as Pr. In all cases, biologically active peptides contain free amino or carboxyl groups. Linkage between the polymer and peptides is generally effected through free amino or carboxyl groups.

The peptides chosen for the purposes of illustration herein are of particular interest in the fields of medicine, agriculture, science, and domestic, as well as industrial applications. They may be enzymes utilized in replacement therapy; hormones for promoting growth in animals, or cell growth in cell culture; or active proteinaceous substances used in various applications, e.g., biotechnology and biological and medical diagnostics. Among the enzymes that can be mentioned are superoxide dismutase, interferon, asparaginease, glutamase, arginase, arginine deaminase, adenosine deaminase ribonuclease, trypsin, chromotrypsin, and papin. Among the peptide hormones that can be mentioned are insulin, calcitonin, ACTH, glucagon, somatosin, somatropin, somatomedin, parathyroid hormone, erthyropoietin, hypothalamic releasing factors, prolactin, thyroid stimulating hormones, endorphins, enkephalins, and vasopressin.

The reaction of the polymer with the peptide to obtain covalently conjugated products is readily carried out. For the purpose of brevity in discussion herein, the polymer is referred to as (P). Where the polymer contains a hydroxyl group, it is first converted to an active carbonate derivative such as para-nitrophenyl carbonate. The activated derivative then is reacted with the peptide in a short period of time under mild conditions producing carbamate derivatives with preserved biological activity.

(Formula 16)

The above reaction and reagent only serve as illustration and are not exclusive; other activating reagents resulting in formation of urethane, or other, linkages can be employed. The hydroxyl group can be converted to an amino group using reagents known in art. Subsequent coupling with peptides through their carboxyl groups results in amide formation.

Where the polymer contains a carboxyl group, it can be converted to a mixed anhydride and reacted with the amino group of the peptide to create a conjugate containing an amide bond. In another procedure, the carboxyl group can be treated with water-soluble carbodiimide and reacted with the peptide to produce conjugates containing amide bonds.

The activity and stability of the peptide conjugates can be varied in several ways, such as changing the molecular ratios of polymer to peptide and by using a polymer of different molecular size. Solubilities of the conjugates can be varied by changing the proportion and size of the polyethylene glycol fragment incorporated in the polymer composition. Hydrophilic and hydrophobic characteristics can be balanced by careful combination of fatty acid and polyethylene glycol moieties.

Set out below are some illustrative modification reactions for polymer-peptide conjugates of the present invention.

I

1. $CH_3(CH_2)_mOH$
2. NaH
3. 1N NaOH

J

1. $CH_3(CH_2)_m(OC_2H_4)_nOH$
2. NaH
3. 1N NaOH/$\emptyset$

K

Z=OTs or Br

L

1. NaH/$\emptyset$
2. $Br(CH_2)_mCOOR$
3. 1N NaOH

M

In the above reaction scheme involving species I, J and K, routes are demonstrated for modifying the hydrophilicity/lipophilicity balance of the conjugating polymer. Ester groups in the conjugating polymer are susceptible to hydrolysis by esterases; the conjugating polymer containing ester groups therefore may be modified to convert the ester groups to ether groups which are more hydrolysis-resistant in character. The reaction scheme involving L and M species illustrates the conversion of hydroxyl groups to carboxylate groups. In this respect, the carboxyl groups will provide carboxylate anion, which is a better stabilizing functionality (forming ionic coordinated complexes) than hydroxyl, which does not form such complexes. Other suitable anion source functional groups for the formation of coordinate ionic complexes involving the polymer species of the present invention include sulfate and phosphate groups.

In general, various techniques may be advantageously employed to improve the stability characteristics of the polymer-peptide conjugates of the present invention, including: the functionalization of the polymer with groups of superior hydrolysis resistance, e.g., the previously illustrated conversion of ester groups to ether groups; modifying the lipophilic/hydrophilic balance of the conjugating polymer, as appropriate to the peptide being stabilized by the polymer; and tailoring the molecular weight of the polymer to the appropriate level for the molecular weight of the peptide being stabilized by the polymer.

The unique property of polyalkylene glycol-derived polymers of value for therapeutic applications of the present invention is general biocompatibility. The polymers have various water solubility properties and are not toxic. They are non-antigenic, non-immunogenic and do not interfere with biological activities of enzymes. They have long circulation in the blood and are easily excreted from living organisms.

The products of the present invention have been found useful in sustaining the biological activity of peptides and may for example be prepared for therapeutic administration by dissolving in water or acceptable liquid medium. Administration is by either the parenteral or oral route. Fine colloidal suspensions may be prepared for parenteral administration to produce a depot effect, or by the oral route.

In the dry, lyophilized state, the peptide-polymer conjugates of the present invention have good storage stability; solution formulations of the conjugates of the present invention are likewise characterized by good storage stability.

The therapeutic polymer-peptide conjugates of the present invention may be utilized for the prophylaxis or treatment of any condition or disease state for which the peptide constituent is efficacious.

In addition, the polymer-peptide conjugates of the present invention may be utilized in diagnosis of constituents, conditions, or disease states in biological systems or specimens, as well as for diagnosis purposes in non-physiological systems.

Further, the polymer-peptide conjugates of the invention may have application in prophylaxis or treatment of condition(s) or disease state(s) in plant systems. By way of example, the peptide component of the conjugate may have insecticidal, herbicidal, fungicidal, and/or pesticidal efficacy amenable to usage in various plant systems.

Still further, the peptide component of the conjugates of the present invention may be antibodies or alteratively antigenic in character, for diagnostic, immunological, and/or assay purposes.

In therapeutic usage, the present invention contemplates a method of treating an animal subject having or latently susceptible to such condition(s) or disease state(s) and in need of such treatment, comprising administering to such animal an effective amount of a polymer-peptide conjugate of the present invention which is therapeutically effective for said condition or disease state.

Subjects to be treated by the polymer-peptide conjugates of the present invention include both human and non-human animal (e.g., bird, dog, cat, cow, horse) subjects, and preferably are mammalian subjects, and most preferably human subjects.

Depending on the specific condition or disease state to be combatted, animal subjects may be administered polymer-peptide conjugates of the present invention at any suitable therapeutically effective and safe dosage, as may readily be determined within the skill of the art, and without undue experimentation.

In general, suitable doses of the formula (1) compounds for achievement of therapeutic benefit, will be in the range of 1 microgram ($\mu$g) to 100 milligrams (mg) per kilogram body weight of the recipient per day, preferably in the range of 10 $\mu$g to 50 mg per kilogram body weight per day and most preferably in the range of 10 $\mu$g to 50 mg per kilogram body weight per day. The desired dose is preferably presented as two, three, four, five, six, or more sub-doses administered at appropriate intervals throughout the day. These sub-doses may be administered in unit dosage forms, for example, containing from 10 $\mu$g to 1000 mg, preferably from 50 $\mu$g to 500 mg, and most preferably from 50 $\mu$g to 250 mg of active ingredient per unit dosage form. Alternatively, if the condition of the recipient so requires, the doses may be administered as a continuous infusion.

The mode of administration and dosage forms will of course affect the therapeutic amounts of the compounds which are desirable and efficacious for the given treatment application.

For example, orally administered dosages are typically at least twice, e.g., 2–10 times, the dosage levels used in parenteral administration methods, for the same active ingredient.

The polymer-peptide conjugates of the invention may be administered per se as well as in the form of pharmaceutically acceptable esters, salts, and other physiologically functional derivatives thereof.

The present invention also contemplates pharmaceutical formulations, both for veterinary and for human medical use, which comprise as the active agent one or more polymer-peptide conjugate(s) of the invention.

In such pharmaceutical and medicament formulations, the active agent preferably is utilized together with one or more pharmaceutically acceptable carrier(s) therefor and optionally any other therapeutic ingredients. The carrier(s) must be pharmaceutically acceptable in the sense of being compatible with the other ingredients of the formulation and not unduly deleterious to the recipient thereof. The active agent is provided in an amount effective to achieve the desired pharmacological effect, as described above, and in a quantity appropriate to achieve the desired daily dose.

The formulations include those suitable for parenteral as well as non-parenteral administration, and specific administration modalities include oral, rectal, buccal, topical, nasal, ophthalmic, subcutaneous, intramuscular, intravenous, transdermal, intrathecal, intra-articular, intra-arterial, sub-arachnoid, bronchial, lymphatic, vaginal, and intra-uterine administration. Formulations suitable for oral and parenteral administration are preferred.

When the active agent is utilized in a formulation comprising a liquid solution, the formulation advantageously may be administered orally or parenterally. When the active agent is employed in a liquid suspension formulation or as a powder in a biocompatible carrier formulation, the formulation may be advantageously administered orally, rectally, or bronchially.

When the active agent is utilized directly in the form of a powdered solid, the active agent may advantageously be administered orally. Alternatively, it may be administered bronchially, via nebulization of the powder in a carrier gas, to form a gaseous dispersion of the powder which is inspired by the patient from a breathing circuit comprising a suitable nebulizer device.

The formulations comprising the active agent of the present invention may conveniently be presented in unit dosage forms and may be prepared by any of the methods well known in the art of pharmacy. Such methods generally include the step of bringing the active compound(s) into association with a carrier which constitutes one or more accessory ingredients. Typically, the formulations are prepared by uniformly and intimately bringing the active compound(s) into association with a liquid carrier, a finely divided solid carrier, or both, and then, if necessary, shaping the product into dosage forms of the desired formulation.

Formulations of the present invention suitable for oral administration may be presented as discrete units such as capsules, cachets, tablets, or lozenges, each containing a predetermined amount of the active ingredient as a powder or granules; or a suspension in an aqueous liquor or a non-aqueous liquid, such as a syrup, an elixer, an emulsion, or a draught.

A tablet may be made by compression or molding, optionally with one or more accessory ingredients. Compressed tablets may be prepared by compressing in a suitable machine, with the active compound being in a free-flowing form such as a powder or granules which optionally is mixed with a binder, disintegrant, lubricant, inert diluent, surface active agent, or discharging agent. Molded tablets comprises of a mixture of the powdered active compound with a suitable carrier may be made by molding in a suitable machine.

A syrup may be made by adding the active compound to a concentrated aqueous solution of a sugar, for example sucrose, to which may also be added any accessory ingredient(s). Such accessory ingredient(s) may include flavorings, suitable preservative, agents to retard crystallization of the sugar, and agents to increase the solubility of any other ingredient, such as a polyhydroxy alcohol, for example glycerol or sorbitol.

Formulations suitable for parenteral administration conveniently comprise a sterile aqueous preparation of the active compound, which preferably is isotonic with the blood of the recipient (e.g., physiological saline solution). Such formulations may include suspending agents and thickening agents or other microparticulate systems which are designed to target the compound to blood components or one or more organs. The formulations may be presented in unit-dose or multi-dose form.

Nasal spray formulations comprise purified aqueous solutions of the active compounds with preservative agents and isotonic agents. Such formulations are preferably adjusted to a pH and isotonic state compatible with the nasal mucus membranes.

Formulations for rectal administration may be presented as a suppository with a suitable carrier such as cocoa butter, hydrogenated fats, or hydrogenated fatty carboxylic acid.

Ophthalmic formulations are prepared by a similar method to the nasal spray, except that the pH and isotonic factors are preferably adjusted to match that of the eye.

Topical formulations comprise the active compound dissolved or suspended in one or more media, such as mineral oil, petroleum, polyhydroxy alcohols, or other bases used for topical pharmaceutical formulations.

In addition to the aforementioned ingredients, the formulations of this invention may further include one or more accessory ingredient(s) selected from diluents, buffers, flavoring agents, disintegrants, surface active agents, thickeners, lubricants, preservatives (including antioxidants), and the like.

In non-therapeutic applications of the present invention, the polymer-peptide conjugate may utilize a covalently bonded or alternatively non-covalent bonding relation between the peptide and polymer components. In addition, associatively related peptide and polymer components may be utilized in administration of therapeutic peptide agents, by appropriate administration methods such as those illustratively described hereinabove in connection with illustratively discussion of covalently bonded polymer-peptide conjugates of the invention.

In such non-therapeutic, associatively related peptide-polymer compositions, the peptide and polymer components may be initially formulated together to provide an enhanced stability and degradation resistance, alternatively, these components may for example be separate parts of a multi-part composition which is mixed at time of use, and which in the absence of associative bonding between the polymer and peptide in the resulting mixture would be susceptible to quick decay or other degradative modality. Regardless of the form of the associatively related peptide and polymer composition, the present invention contemplates a relational association which enhances some characteristic or aspect of the peptide or otherwise enhances the utility of same, relatively to the peptide component in the absence of such associative polymer.

Accordingly, the present invention contemplates the provision of suitable polymers for in vitro stabilization of peptides in solution, as a preferred illustrative application of non-therapeutic application. The polymers may be employed for example to increase the thermal stability and enzymic degradation resistance of the peptide. Enhancement of the thermal stability characteristic of the peptide via conjugation in the manner of the present invention provides a means of improving shelf life, room temperature stability, and robustness of diagnostic and research reagents and kits, e.g., immunoassay kits. By way of specific example, alkaline phosphatase may be covalently or associatively coupled to a suitable polymer in accordance with the invention, to impart stability to such phosphatase when used as a reagent in kits for colorimetric detection of antibody or antigen in biological fluids.

The following Examples are provided to illustrate the present invention, and should not be construed as limiting thereof.

5. EXAMPLES

LCRF-amphiphilic polymer conjugate can be synthesized and tested for CCK-releasing activity. The LCRF conjugate can then be evaluated for resistance to proteolysis. Physiological and behavioral effects can be confirmed by in vivo animal studies.

5.1 Synthesis of an LCRF Amphiphilic Polymer Conjugate

By using amphiphilic oligomers or polymers of different size and chemical composition, the peptide conjugate absorption and partitioning properties can be altered. It is preferred that the polymers that will be coupled to the LCRF peptide must not interfere with receptor binding. The precise nature of the interaction between LCRF and its receptor is not known, but two observations concerning the interaction have been made: residues 11–25 are crucial for the interaction, and cleavage between residues 19 and 20 destroys binding activity. Therefore, we will use a hydrolyzable linker at K19 to protect the peptide from trypsin proteolysis.

The conjugates of the invention have two components (PEG and alkyl chain) that will endow the LCRF with two useful properties. First, using a larger, branched oligomer at the N-terminus prevents uptake into the bloodstream from the gut. We will add a 5–10 kDa oligomer to the N-terminus for this purpose, since molecules with a molecular weight of greater that 4 kDa do not cross the gut wall into the bloodstream, but are retained in the lumen. (Parlesak, A., Bode, J. C., Bode, C. "Parallel Determination of Gut Permeability in Man with M(r) 400, M(r) 1500, M(r) 4000 and M(r) 10,000 Polyethylene Glycol," *Eur. J. Clin. Chem. & Clin. Biochem.*, 32: 813–820 (1994) (the disclosure of which is incorporated herein in its entirety)). Second, the hydrophobic alkyl chain will be able to integrate into cell membranes of the gut epithelium, bringing the peptide in close proximity to its target receptor on the epithelial cell surface. It is preferable to attach the PEG/alkyl conjugate at the N-terminus, far from residues implicated in receptor binding.

The first 35 residues of LCRF$^{iii}$ can be synthesized by solid phase methods and obtained from commercial suppliers. The LCRF conjugation techniques will follow three basic designs, summarized in FIG. 2.

Figure 2:
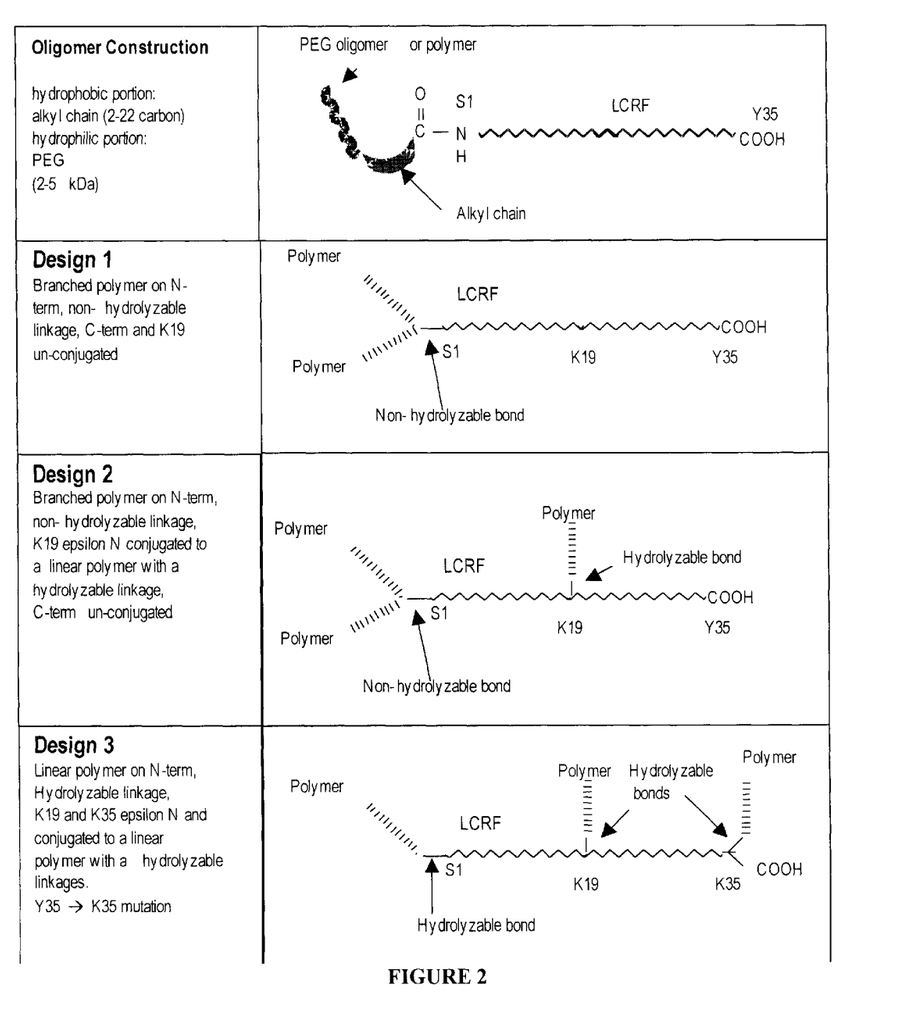
FIG. 2 shows three basic designs for LCRF conjugation techniques.
Figure 3:
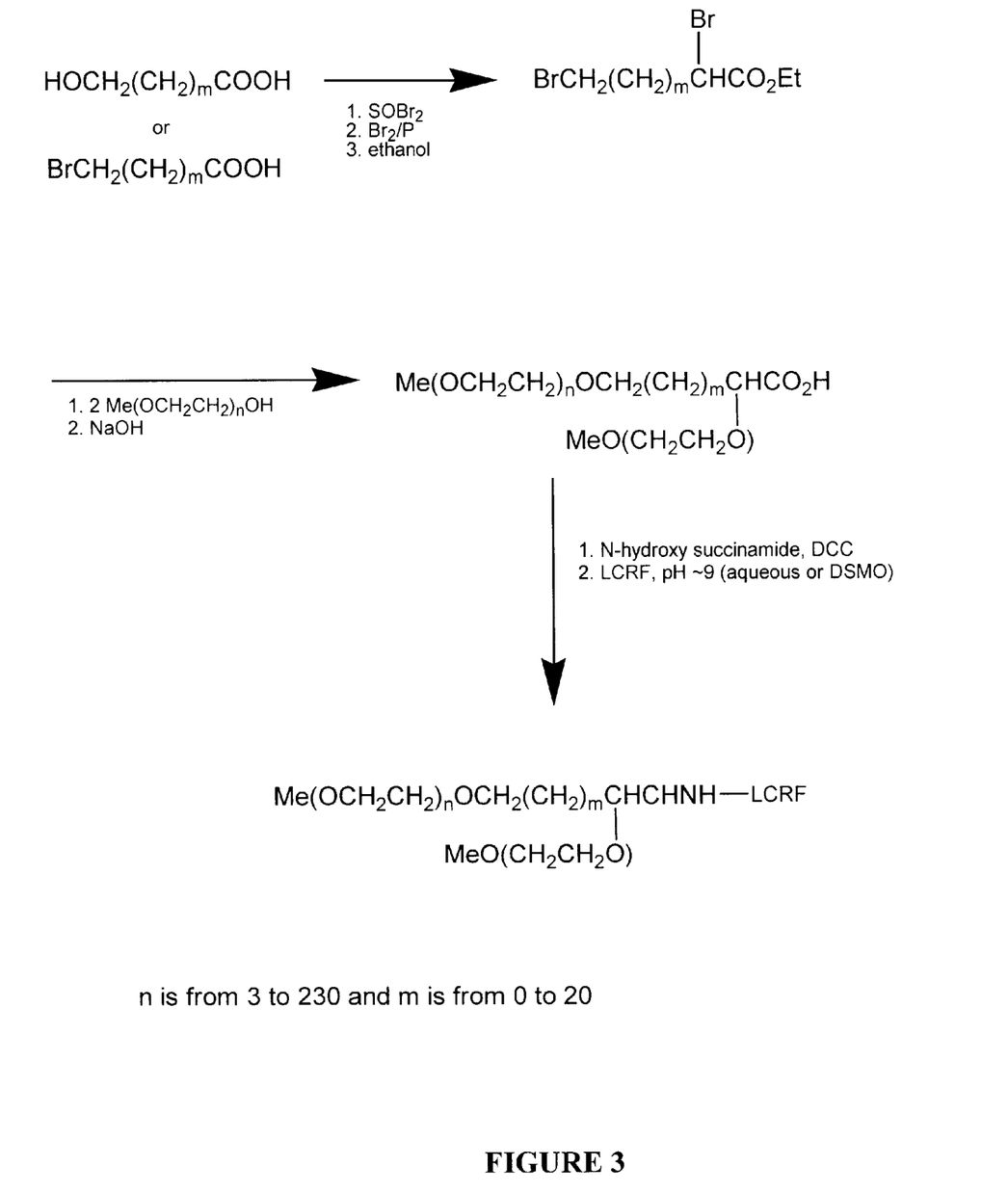
FIG. 3 shows the basic synthetic scheme for preparing the polymers according to the invention.

LCRF contains two reactive amino groups that can be used for linking the conjugate—the amino terminus and a lysine sidechain. A first conjugate (Conjugate 1) can utilize a branched oligomer having a total average molecular weight of 4–10 kDa attached to the N-terminus of LCRF using a non-hydrolyzable linker. There are three key features of this conjugate. First, the oligomers at the N-terminus are positioned distal to the known receptor-binding domain of LCRF and are thus unlikely to impair its biological potency. Second, the branched oligomer on the N-terminus will provide steric hindrance to aminopeptidases that would otherwise digest the peptide. Third, the branched oligomers provide both extreme water solubility and greatly increased size of the LCRF conjugate, which prevents passage of the peptide through the epithelial wall of the small intestine.

Conjugate 2 can utilize the N-terminal conjugate described for Conjugate 1 and a second, linear conjugate attached to the epsilon amino group of K19. This linear oligomer can be attached with a hydrolyzable bond so that, over time, the oligomer will be hydrolyzed off to permit the LCRF to bind its receptor. K19 is in the approximate center of the putative receptor-binding sequence. The key features of Conjugate 2, in addition to those described for Conjugate 1, are the addition of a hydrolyzable oligomer at K19 that will protect against trypsin hydrolysis. Second, the hydrolyzable linkage of the oligomer should enable appropriate receptor binding. Third, the slow hydrolysis of the oligomer at K19 (expected $T_{1/2}$ of 30–60 min) may provide an extended time of action of the LCRF. Design 3 will have a conjugate added at the C-terminus, N-terminus, and at K19. The C-terminal residue (tyrosine) is changed to lysine, thus providing a third site for conjugation. This mutation is not expected to alter receptor binding, as the binding domain is at least 10 residues from residue 35. The balance of amphiphilicity is achieved using three linear polymers instead of a branched oligomer. The addition of a hydrolyzable oligomer at the C-terminus will provide resistance to degradation by carboxypeptidases. The removal of all the oligomers by hydrolysis will regenerate the active LCRF for full biological activity. Hydrolysis (expected $T_{1/2}$ of 30–60 min) of the oligomers may provide extended action of the LCRF.

The synthetic chemistry for LCRF conjugate synthesis is shown in FIG. 3. Oligomeric carboxylic alkanols are activated with bromine and esterified. Oligomeric PEG is then coupled to the activated alkane oligomers. Coupling of the PEG/alkane carboxylic acid to the free amino group of the peptide, is achieved with N-hydroxysuccinamide in aqueous solution at a pH where the amino group is nucleophilic. Previously synthesized and purified oligomers are activated and coupled to LCRF in variable reaction conditions that permit the attachment of oligomers at certain sites (N-terminus, C-terminus or K19). A sequence of conjugation reactions and product purifications can also be used to achieve specific conjugation patterns. Selectivity of the N-terminal amino group over the lysine side chain will be achieved by choosing the pH of the reaction medium. Coupling to the N-terminus (pKa ~8) is carried out a pH ~9 where the epsilon amino group (pKa ~10.6) is still protonated.

By varying the relative length of the alkane (hydrophobic) and PEG (hydrophilic) components, the amphiphilicity and solution structure of the conjugate can be optimized.

The reaction mixture is purified on a preparative HPLC column (C-18) with a solvent gradient system made of isopropanol/water (0.1% trifluoroacetic acid). The solvent is evaporated under reduced pressure and temperature below 20° C. to give dry products. Purity of the product is analyzed by reverse phase HPLC and mass spectrometry. Cell-based assays provide a rapid means of confirming the biological activity (e.g., the ability of the conjugates to elicit CCK release from CCK-releasing cells) of the LCRF conjugates.

Cell based assays can be used to compare the effect of treatment with out conjugates to treatment with vehicle. Native LCRF elicits about a 300% increase in CCK secretion. Our objective is to elicit at least a 200% increase in CCK secretion with our conjugates. Six assays per experiment are expected to provide statistically significant results.

Native CCK Cells can be prepared as follows: Intestinal mucosal cells are prepared from 200–225 g male and female Sprague-Dawley rats. After sacrifice, the proximal 10 cm of small intestine, beginning 2 cm distal to the pylorus, are quickly removed and immediately placed in saline and washed. The intestine is cut into short lengths, everted, and placed in phosphate buffered saline (PBS). The mucosal surface is rinsed twice with PBS and placed in trypsin-free dissociation media at 37° C. with gentle agitation for 2 minutes. The solution is removed and replaced with fresh dissociation media and incubated for 10 more minutes with gentle agitation. The remaining suspension is filtered (450 μm) and the effluent centrifuged (1000 rpm, 3 minutes). The pellet is resuspended in Hank's balanced salt solution with HEPES (10 mM; pH 7.4)(HHBSS) and centrifuged as above. The pellet is resuspended in 5 ml HHBSS and divided into aliquots for testing.

Activity of conjugates can be confirmed as follows: CCK cells are incubated with test compounds (or vehicle) for between 5 and 40 minutes. The incubation is stopped by placing the cells in ice, centrifuging the cells, and removing supernatant. For conjugates containing hydrolyzable linkers, incubations will be stopped at 5, 10, 15, 20, 30 and 40 minutes. For conjugates without a hydrolyzable linker, only one time point (15 minutes) need be used. Supernatant is used for the RIA measurement of CCK described below. 50 μl of the supernatant is assayed by HPLC and MALDI-TOF mass spectrometry to measure the amounts of LCRF conjugates remaining.

A radioimmunoassay (RIA) can be used for measuring CCK secretion. (Mangel, A. W., Prpic, V., Wong, H., et al. "Phenylalanine-stimulated Secretion of Cholecystokinin is Calcium Dependent," *A. J. Physiol.*, 268: G90–94 (1995) (the disclosure of which is incorporated herein in its entirety)). Secretion is measured from CCK-releasing cells plated in 24-well microtitre plates. Cells are incubated at 37° C. and washed with HHBSS containing HEPES (10 mM, pH 7.4). 0.5 ml of buffer is added with or without test agents to cells for times ranging from 5 to 40 minutes. 350 μl are removed, centrifuged and placed on ice or frozen. 300 μl of the sample will be used for the RIA. The RIA is performed in PBS containing HEPES (10 mM, pH 7.5), 0.1% gamma globulin, with 0.01% $NaN_3$. 50 μl of sample are added to 200 μl of the RIA buffer and 100 μl of a 1:80,000 dilution of a rabbit CCK antibody (OAL-656). 100 μl of $^{125}$I-CCK-8 (3,000–4,000 cpm) are then added to the tubes at 4° C. for 12 hours. Samples are treated with goat anti-rabbit IgG sepharose CL4B beads for one hour with gentle agitation. The sepharose beads are then pelleted by brief centrifugation and the pellet is aspirated. The pellet is re-suspended in 0.5 ml of HEPES buffered saline, and the beads are pelleted once again. Then the beads are removed and washed, and the pellet is counted on a gamma counter for 5 minutes. Unconjugated LCRF causes about a 300% increase in CCK secretion from native CCK and STC-1 cells, and will be used as a positive control for cell assays.

In the case of test compounds with hydrolyzable conjugates, CCK release (RIA) can be correlated with conjugate hydrolysis (HPLC-MS).

The precise nature of the conjugate can be optimized to provide desired properties. The N- and C-terminal conjugation approach will be tested to see whether N- or C-terminal conjugation, or both, provides the best protection and biological activity.

When LCRF is infused into the duodenum of rats, a biphasic dose-response of curve of pancreatic protein output is observed, with higher doses of LCRF leading to decreased pancreatic protein output. Suitable conjugate concentrations can be determined by those of skill in the art in view of the instant disclosure and may range from 1 to 1000 nM.

CCK secretion is thought to be regulated by negative feedback inhibition. LCRF is produced constitutively in the duodenum in rats, and in response to nutrients in humans. When food is absent, LCRF is degraded by proteases in the duodenum. Since duodenal infusion of trypsin inhibitors is sufficient to cause an increase in CCK release in rats, we propose that protection from trypsin cleavage will be sufficient to protect the LCRF conjugation from proteolytic digestion. (Green, G. M., Taguchi, S., Friestman, J., Chey, W. Y., Liddle, R. A. "Plasma Secretin, CCK, and Pancreatic Secretion in Response to Dietary Fat in the Rat," *Am. J. Physiol.*, 256: G1016–1021 (1989)). We have used our conjugation technique successfully to protect calcitonin and insulin from proteolysis.

The stability of conjugated LCRF in intestinal environments can be determined by examining the stability of the peptides to the proteolytic enzymes trypsin, pancreatic elastase, and chymotrypsin over 40 minutes, a typical gut transition time. Conjugated LCRF solutions are incubated at 37° C. (0.1% Tween 20 [w/v], 10 mM $NaHPO_4$, pH 7.4) and proteases are added. Tween (0.1%) will be added to solubilize the peptides if required. The proteolysis is stopped by adjusting pH to 2–3. The resultant samples are separated by HPLC using a 5 μm, C-18 column; and eluted for 25 minutes at 0.5 ml/min with a linear gradient of 90% $H_2O$/0.1% trifluoroacetic acid and 10% 2-propanol increasing to 60% 2-propanol.

The stability of conjugated LCRF in stomach can be determined by examining the stability of the peptides to pepsin. Pepsin degradation of conjugated LCRF is determined in simulated gastric fluid (33 mM NaCl, pH 1.2). Peptide solutions are incubated at 37° C. and pepsin is added. Proteolysis is stopped by raising pH to 7.0–7.5.

HPLC can be used to monitor the proteolysis. Area under absorbance peaks (280 nm) is integrated to follow the rate of proteolysis over time. Decrease in the integrated area of the peak arising from the uncleaved LCRF conjugate will be used to monitor the rate of hydrolysis. HPLC separation will be done as described above in Specific Aim 1 for conjugated LCRF purification.

Chymotryptic cleavage sites exists at residues Y17 and Y20. If chymotrypsin rapidly cleaves the peptide, we will add a protecting PEG group to the tyrosine hydroxyl group with a linkage that slowly hydrolyses at pH 7.4. Elastase cleavage sites exist at residues 5, 10, 29, 30 and 31. These residues are outside the region (11–25) identified as crucial for receptor binding. If required, protection from gastric fluid will be provided by enteric coating, a well-established technology in the pharmaceutical industry.

In a preferred aspect of the invention, the conjugates provide an increase over basal secretion of at least 200% in CCK release upon treatment with conjugated LCRF, as measured by RIA. Native LCRF causes about a 300% increase in CCK secretion from native CCK cells and will be used as a positive control for these studies.

Moreover, it is preferred that the conjugates experience less than 70% proteolysis of the LCRF conjugate, upon exposure to serine proteases (pH 7.4) for 40 minutes. It is also preferred that the conjugates experience less than 10% proteolysis of the enteric-coated LCRF conjugate, upon exposure to simulated gastric fluid for 40 minutes.

Those of skill in the art can, with the aid of the present disclosure, confirm the physiological and behavioral consequences related to feeding and obesity in animal models and human subjects. Rat intestine is used as the source of tissue for purification of mucosal CCK cells. Rats are sacrificed for the sole purpose of collecting intestinal tissue. Following sacrifice, the intestine is surgically removed and washed and intestinal cells are prepared by collagenase and EDTA dispersion. Male and female Sprague-Dawley rats, 2.5–3 months old weighing 250–300 g will be the source of the CCK cells. Approximately 48 rats will be required for the proposed study to yield meaningful results. Considerable work has been done on the regulation of CCK secretion in rats. Each rat should provide enough CCK cells for one experiment. Rats are sacrificed for the collection of intestinal tissue. The method of euthanasia is preferably $CO_2$ narcosis, for which rats are placed into an air-tight cage containing $CO_2$. This method is consistent with the recommendations of the Panel on Euthanasia of the American Veterinary Medical Association.

---

---

What is claimed is:

1. A compound of the formula:

where n is from 3 to 230 and m is from 0 to 20.

2. A compound of the formula:

$$\text{Me(OCH}_2\text{CH}_2)_n\text{XCH}_2(\text{CH}_2)_m\overset{|}{\underset{\text{Me(OCH}_2\text{CH}_2)_n\text{X}}{\text{CHCHNH}}}\text{—LCRF}$$

where n is from 3 to 230 and m is from 0 to 20 and X is selected from the group consisting of N, O or S.

3. A compound of the formula:

$$\text{Me(OCH}_2\text{CH}_2)_n\text{OCH}_2(\text{CH}_2)_m\overset{|}{\underset{\text{Me(OCH}_2\text{CH}_2)_n\text{O}}{\text{CHCHNH}}}\text{-Protein}$$

where n is from 3 to 230 and m is from 0 to 20.

4. A compound of the formula:

$$\text{Me(OCH}_2\text{CH}_2)_n\text{XCH}_2(\text{CH}_2)_m\overset{|}{\underset{\text{Me(OCH}_2\text{CH}_2)_n\text{X}}{\text{CHCHNH}}}\text{-Protein}$$

where n is from 3 to 230 and m is from 0 to 20 and X is selected from the group consisting of N, O or S.

5. A compound comprising:
   a luminal cholecystokinin releasing factor polypeptide comprising a lysine residue;
   an oligomeric moiety attached to the N-terminus of the luminal cholecystokinin releasing factor polypeptide; and
   an oligomeric moiety attached to the lysine residue;
   wherein, upon administration to a subject, said compound integrates into a cell membrane of the gut epithelium of the subject, wherein, the luminal cholecystokinin releasing factor polypeptide binds with a target receptor on the epithelial cell surface to provide release of cholecystokinin.

6. The compound according to claim 5, wherein the oligomeric moiety attached to the N-terminus of the luminal cholecystokinin releasing factor peptide is a branched oligomeric moiety.

7. The compound according to claim 6, wherein the branched oligomeric moiety has the following formula:

$$\text{Me(OCH}_2\text{CH}_2)_n\text{OCH}_2(\text{CH}_2)_m\overset{|}{\underset{\text{Me(OCH}_2\text{CH}_2)_n\text{O}}{\text{CHCHNH}}}\text{—}$$

where n is from 3 to 230 and m is from 0 to 20.

8. The compound according to claim 6, wherein the branched oligomeric moiety has the following formula:

$$\text{Me(OCH}_2\text{CH}_2)_n\text{XCH}_2(\text{CH}_2)_m\overset{|}{\underset{\text{Me(OCH}_2\text{CH}_2)_n\text{X}}{\text{CHCHNH}}}\text{—}$$

where n is from 3 to 230 and m is from 0 to 20 and X is selected form the group consisting of N, O or S.

9. The compound according to claim 6, wherein the branched oligomeric moiety has a total average molecular weight of 4,000 to 10,000 Daltons.

10. The compound according to claim 5, wherein the oligomeric moiety is attached to the N-terminus using a non-hydrolyzable linker.

11. The compound according to claim 6, wherein the branched oligomeric moiety is attached to the N-terminus using an non-hydrolyzable linker.

12. The compound according to claim 5, wherein the oligomeric moiety attached to the N-terminus of the luminal cholecystokinin releasing factor polypeptide has a total average molecular weight of 4,000 to 10,000 Daltons.

13. The compound according to claim 5, wherein the oligomeric moiety is attached to the lysine residue using a hydrolyzable bond.

14. The compound according to claim 5, wherein the oligomeric moiety attached to the lysine residue is a linear oligomeric moiety.

15. The compound according to claim 14, wherein the linear oligomeric moiety is attached to the lysine residue using a hydrolyzable bond.

16. The compound according to claim 5, further comprising a lysine residue at the C-terminus of the luminal cholecystokinin releasing factor polypeptide.

17. The compound according to claim 16, further comprising a linear oligomeric moiety attached to the lysine residue at the C-terminus of the luminal cholecystokinin releasing factor polypeptide.

18. A compound comprising:
   a luminal cholecystokinin releasing factor polypeptide comprising a first lysine residue and a second lysine residue, wherein, the second lysine residue is at the C-terminus of the luminal cholecystokinin releasing factor polypeptide;
   a branched oligomeric moiety attached to the N-terminus of the luminal cholecystokinin releasing factor polypeptide using a non-hydrolyzable linker;
   a linear oligomeric moiety attached to the first lysine residue of the luminal cholecystokinin releasing factor polypeptide using a hydrolyzable bond; and
   a linear oligomeric moiety attached to the second lysine residue at the C-terminus of the luminal cholecystokinin releasing factor polypeptide;
   wherein, upon administration to a subject, said compound integrates into a cell membrane of the gut epithelium of the subject, wherein, the luminal cholecystokinin releasing factor polypeptide binds with a target receptor on the epithelial cell surface to provide release of cholecystokinin.

19. The compound according to claim 18, wherein the branched oligomeric moiety has the following formula:

$$\text{Me(OCH}_2\text{CH}_2)_n\text{OCH}_2(\text{CH}_2)_m\overset{|}{\underset{\text{Me(OCH}_2\text{CH}_2)_n\text{O}}{\text{CHCHNH}}}\text{—}$$

where n is from 3 to 230 and m is from 0 to 20.

20. The compound according to claim 18, wherein the branched oligomeric moiety has the following formula:

$$\text{Me(OCH}_2\text{CH}_2)_n\text{XCH}_2(\text{CH}_2)_m\overset{|}{\underset{\text{Me(OCH}_2\text{CH}_2)_n\text{X}}{\text{CHCHNH}}}\text{—}$$

where n is from 3 to 230 and m is from 0 to 20 and X is selected from the group consisting of N, O or S.

21. The compound according to claim 18, wherein the branched oligomeric moiety has a total average molecular weight of 4,000 to 10,000 Daltons.

* * * * *